Figure 1:
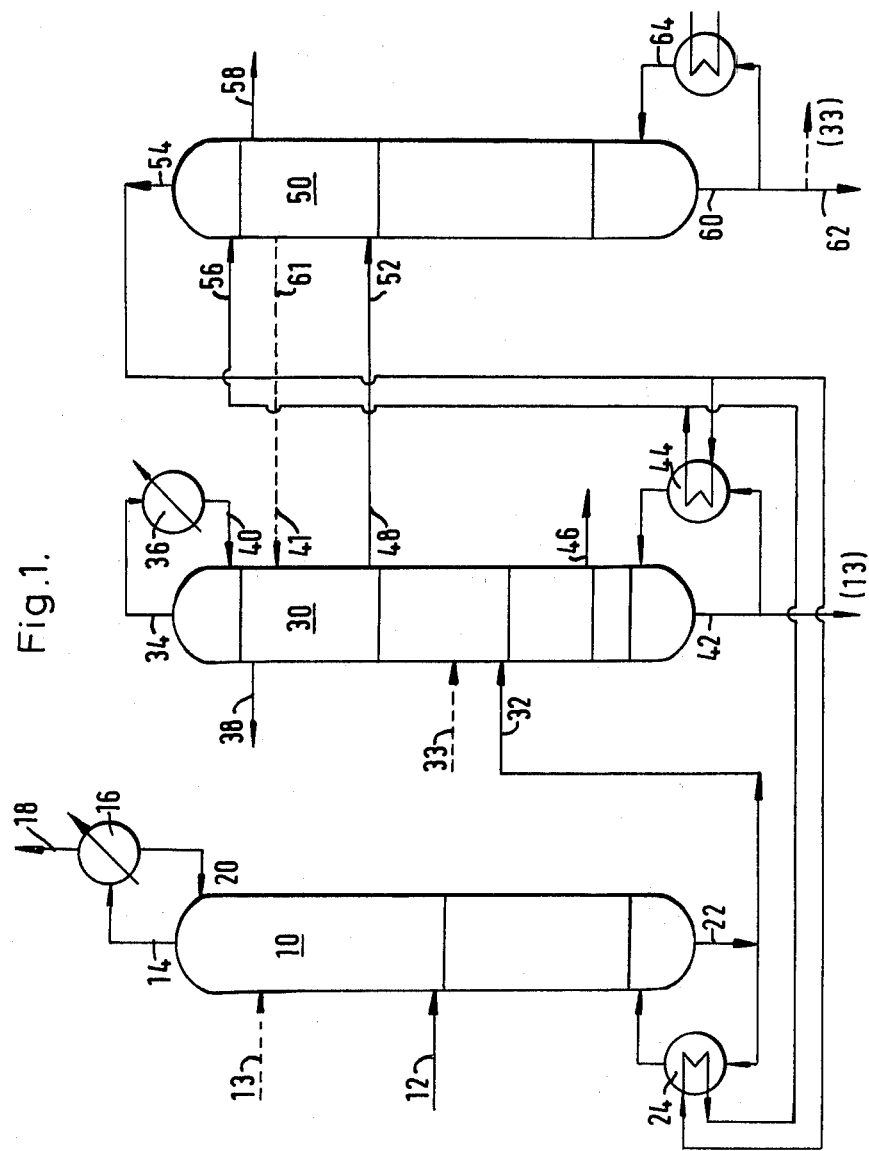

United States Patent [19]

Pinto

[11] 4,210,495

[45] Jul. 1, 1980

[54] METHANOL DISTILLATION PROCESS

[75] Inventor: Alwyn Pinto, Stockton-on-Tees, England

[73] Assignee: Imperial Chemical Industries Limited, London, England

[21] Appl. No.: 877,737

[22] Filed: Feb. 14, 1978

[30] Foreign Application Priority Data

Mar. 11, 1977 [GB] United Kingdom ............... 10403/77

[51] Int. Cl.² ........................ B01D 3/14; C07C 29/26
[52] U.S. Cl. ........................................ 203/22; 203/18; 203/25; 203/73; 203/81; 203/DIG. 19; 203/DIG. 23
[58] Field of Search ................... 203/18, DIG. 19, 99, 203/21, 25, 26, 24, 22, 96, 97, 92, 93, 76, 79, 83, 85, 74, 77, 81, DIG. 23; 568/913; 260/449.5

[56] References Cited

U.S. PATENT DOCUMENTS

| | | | |
|---|---|---|---|
| 2,115,401 | 4/1938 | Shiffler | 203/24 |
| 2,152,164 | 3/1939 | Wentworth | 203/26 |
| 3,230,156 | 1/1966 | Katzen | 203/37 |
| 3,254,024 | 5/1966 | Huckins et al. | 203/25 |
| 3,391,064 | 7/1968 | Akell | 203/83 |
| 3,406,100 | 10/1968 | Karafian | 203/78 |
| 3,568,457 | 3/1971 | Briggs et al. | 203/26 |
| 3,597,465 | 8/1971 | Karafian et al. | 260/449.5 |
| 4,013,521 | 3/1977 | Scott | 203/85 |

*Primary Examiner*—Wilbur L. Bascomb, Jr.
*Attorney, Agent, or Firm*—Cushman, Darby & Cushman

[57] ABSTRACT

Purified methanol is produced by distilling a water methanol mixture in (a) a first column from which is taken a product methanol stream at an upper level, weakly aqueous methanol as a side stream and water as bottoms and (b) a second column in which that weakly aqueous methanol is separated into an overhead product stream and aqueous methanol bottoms. The first column may be preceded by a preliminary volatiles-removal column. The process is economical in heat consumption, especially when methanol vapor from the second column is heat-exchanged with the feed or bottoms of the first column.

14 Claims, 3 Drawing Figures

METHANOL DISTILLATION PROCESS

This invention relates to methanol and in particular to a distillation process and apparatus for producing purified methanol at high thermal efficiency.

Crude methanol as produced by catalytic synthesis usually contains water and small quantities of organic compounds boiling below and above the boiling point of methanol. Distillative separation of these constituents requires a large input of low grade heat, which is conveniently supplied by heat exchange with low pressure steam or with suitable warm gases in the synthesis plant or synthesis gas generation plant. An example of such a distillation, described in U.K. specification No. 1280438, includes a preliminary column in which impurities more volatile than methanol are removed overhead; a first column in which product methanol is separated overhead, water is separated as bottoms and an aqueous methanol side stream is taken off; and a second column in which the aqueous methanol side stream is separated into an overhead methanol stream that is recycled to the first column and water bottoms that are discarded. Such a process involves column reboiler heating by warm crude synthesis gas and/or by a liquid (such as pressurised water) that has been heated by heat exchange with reacted synthesis gas.

We have now realised that the distillation sequence described in U.K. No. 1280438 can be modified to improve its thermal economy by taking from the first column an aqueous methanol side stream of higher methanol content and by controlling the bottoms composition of the second column at a lower water content.

According to the invention a process for producing purified methanol by distillation comprises the steps of (a) feeding a water-methanol mixture to a first distillation column, taking a product methanol stream from an upper level, taking aqueous methanol containing at least 95% w/w of methanol as a side stream and taking a predominantly water stream as bottoms; and (b) feeding the aqueous methanol side stream to a second distillation column, taking a product methanol stream from an upper level and taking as bottoms a stream containing less than 60% w/w of water.

This combination of steps can be put to use in a number of ways. In its simplest form the first column includes an overhead off-take for components more volatile than methanol. This two-column system is expected to find application chiefly in the production of fuel-grade methanol.

In a form of more general application the two columns are preceded by a preliminary column ("topping" or "extraction") from which components more volatile than methanol are taken overhead and aqueous methanol bottoms is fed to the first column of the process of the invention.

Three particular forms of the invention afford especially high thermal efficiency.

In a form (see FIG. 2) capable of using very low grade heat, such column is operated at a relatively low pressure, suitably in the range 1–20 psig, measured at the top. It will be appreciated that the heat consumption will be significantly lower at locations substantially above sea level. Since the water content and thus also the boiling point of the bottoms in the first column is higher than in the second column, it is convenient to pass fresh heat-carrying fluid, whether process gas or low pressure steam or a liquid, to the first column reboiler, and then to pass the partly cooled fluid leaving that reboiler to the reboiler of the second column or to divide it and pass it to the reboilers of the preliminary and second columns in parallel. This form of the invention is especially useful in combination with a methanol production process including recovery of high grade heat and medium grade heat during synthesis gas generation and methanol synthesis, since it makes use of heat that otherwise cannot be conveniently recovered.

In a form (see FIG. 1) affording very high thermal efficiency but requiring a source of higher grade heat, the columns are heated by passing fresh heat-carrying fluid to the reboiler of the second column and passing methanol vapour from the top of that column in heat exchange in the reboilers of the first and/or the preliminary column (if used). For the effective heating of the bottoms of the preliminary and/or first column the methanol vapour may be superheated or may be compressed before coming into heat exchange with these bottoms liquids. Most conveniently, however, the second column is operated at a pressure high enough to ensure that its overhead vapour is not enough to cause boiling of those bottoms liquids. Suitably the column pressure is higher by 70–120 psi than that of the column or columns to be heated by its overhead vapour. If a smaller difference is desirable, the preliminary and/or first column can be in part heated from an external source, conveniently by direct steam. A suitable pressure in the low pressure column or columns is in the range 1–20 psig, measured at the top.

In a third form of the invention (see FIG. 3) employing external heat at a grade intermediate between that of the first and second forms, the columns are heated by passing fresh heat-carrying fluid to the reboiler of the second column and passing methanol vapour from the top of that column in heat exchange with water-methanol mixture fed to the first column and/or (if one is used) to the preliminary column. In addition, the methanol vapour can be passed in heat exchange in the reboiler of a preliminary column. The heat exchange can be applied to the feed stream only or to the mixture of feed and plate-liquid, for example by circulating the plate liquid out to the heat exchanger in the feed line, or by delivering the feed to the plate as unheated liquid and circulating mixed plate liquid out to a heat exchanger and then back on to the plate. Again the methanol vapour may be superheated or may be compressed before coming into the heat exchange, but most conveniently the second column pressure is high enough to ensure that its vapour is hot enough, suitably higher by 20–70 psi than the pressure of the first column. The temperature of the methanol vapour is chosen in relation to the pressure and composition of the first column feed preferably such that the feed is partly vaporised before entering the first column. This decreases the externally supplied bottoms heat load in the first column and makes it possible to add heat to the feed with a lower temperature difference than would be required if the feed were to be maintained in the liquid state.

The crude methanol feed to the process, whether or not it includes a preliminary column, may include water at for example 8–30% w/w and there may be, alternatively or additionally, a feed of water at a level above crude methanol feed level, sufficient to produce a bottoms liquid containing over 40, for example 40–60 or even 80–95% w/w of water. The effect of water is to increase the relative volatility of impurities such as ketones and higher alcohols to such an extent that they pass out overhead with the impurities (such as dimethyl ether) that are of lower boiling point than methanol. Usually such a withdrawal of volatiles, especially if there is a separate water feed, is effected in a preliminary column.

The first column effects the bulk of the water-methanol and separation. The side stream suitably contains more than 98% w/w methanol, preferably over 99% w/w. The methanol flow rate of the side stream is suitably 30 to 70% by mols of the methanol in the crude or topped or water-extracted methanol fed to this column. There can be a feed of recycled bottoms from the second column and/or recycled pure or near-pure methanol from that column, but this is not counted when calculating the rate of flow of the side stream.

The second column separates the side stream aqueous methanol into an overhead stream of substantially pure methanol and a bottoms stream containing methanol, water and ethanol. The water content of the bottoms stream is preferably under 40% w/w, especially under 20% w/w. The composition of the bottoms stream is typically similar to that of the feed to the first column and accordingly that stream can be recycled to the first column at an appropriate level: part of it can be purged in order to avoid returning too much ethanol. Although the methanol content of this bottoms stream is relatively high, its flow rate can be and preferably is controlled to contain only 0.1 to 1.0% of the methanol fed to the process. If desired, a proportion of overhead methanol condensate can be recycled to an upper level of the first column in order to increase the reflux ratio therein.

It will be appreciated that the nature of the heat-carrying fluids used is usually a matter of detailed design, depending on the design of the methanol synthesis and synthesis gas generation steps that precede the distillation. The following fluids are quoted by way of example.

When the second column is operated at a pressure in the range 1–20 psig the source of heat for its reboiler is preferably saturated or slightly superheated stream at a pressure under 50 psig, especially in the range 15 to 40 psig. Alternatively it is a liquid such as pressurised water at a temperature in the range 125° to 160° C. If it is process gas it is preferably at a pressure in the range 10 to 30 atm. abs and a temperature in the range 125° to 160° C.; preferably also it contains 30–70% v/v of steam, and is crude synthesis gas.

When the second column is operated at a pressure 70–120 psig higher than that of the column or columns to be heated by its overhead vapour, the source of heat for its reboiler is preferably saturated or slightly superheated steam at a pressure over 30 psig, especially in the range 40 to 60 psig. If it is a liquid, the liquid temperature is over 140° C. and suitably in the range 160° to 200° C. If it is process gas, its pressure is preferably in the range 10 to 30 atm. abs., its temperature 140° to 200° C. and again it contains 30–70% v/v of steam.

When the second column is operated at a pressure 20–70 psi higher than that of the first column, the source of heat is preferably saturated or slightly superheated steam at a pressure over 5 psig, especially in the range 15–30 psig. If the source of heat is a liquid, (such as pressurised water) the liquid temperature is over 110° C. and suitably in the range 120°–150° C. If it is process gas, its pressure is preferably in the range 5–60 atm. abs., its temperature 120°–150° C. and it preferably contains 30–70% v/v of steam. In this third form of the process, when the first column is operated (as is preferred) at a pressure in the range 1–20 psig, the source of heat for its reboiler is preferably saturated or slightly superheated steam at a pressure in the range 20–50 psig. Such steam can be used by direct injection, if desired, instead of or in addition to indirect heat exchange in a reboiler. The heating medium can alternatively be a liquid at a temperature in the range 130°–170° C. or process gas at a pressure preferably in the range 10–60, for example 10–30 atm. abs., a temperature in the range 130°–170° C. and preferably containing 30–70% v/v of steam.

Crude synthetic methanol normally contains small quantities of ethanol, ketones and higher alcohols. Such of these compounds (especially ethanol) as are not removed overhead in the preliminary "topping" or "extraction" column are preferably removed as a purge stream in the first column at a level below the feed. This is desirable if there is no purge of ethanol from the second column, especially when the whole of the bottoms liquid from the second column is recycled to the first column, since that liquid contains substantially all the ethanol in the feed to the second column. In order to maximise the ethanol content and minimise the methanol content of the first column purge stream, the feed to the first column can be misplaced upwards, that is, at a level at which, when the column is in equilibrium operation, the water content is lower than in the feed, so as to produce over a region of the column below the feed level a substantially constant methanol to water ratio; the purge stream enriched in ethanol is taken near, especially just below, the end of the region remote from the feed level. Such a process using a misplaced feed is the subject of our U.K. Pat. No. 1,373,159.

The combination of the two or three columns as required by the process described above, whether alone or with also the plant for the synthesis process and possibly also the synthesis gas generation section described below, constitute the apparatus according to the invention. The columns may be of the tray type or packed type or a combination.

The process of the invention is especially suitable for purifying crude methanol made by catalytic synthesis from carbon oxides and hydrogen. If the synthesis is of the older type, at pressures above 200 atm. abs., and temperatures in the range 300°–400° C., over a zinc-chrome catalyst, the process preferably includes water-extraction in the preliminary or first column, owing to the relatively high content of impurities of low solubility in water. If the synthesis is of the recently developed type at under 300° C., at pressures usually in the range 30–120 atm. abs. but possibly up to 400 atm. abs., and using a copper-containing catalyst, the preliminary column need not provide water-extraction. If the intended product purity specification is not too stringent, the first column can provide the topping function. Since synthesis over a copper-containing catalyst preferably uses a gas containing more carbon dioxide (1–20, especially 3–12% v/v) than the gas used in the older process (preferably under 1%), the crude methanol produced by it typically contains a substantial proportion of water, commonly in the range 8–30% w/w. Such a water content is usually sufficient for a simple topping column, especially since the content of impurities of low water solubility in the crude methanol is much lower than in that produced by the older process.

Typical processes using a copper-containing catalyst are described in our U.K. Pat. Nos. 1,010,871 (copperzinc-chrome catalyst) and 1,159,035 (copper-zinc—Group II–IV oxide, especially copper-zinc-aluminium, catalyst). Processes using catalysts containing oxides of manganese, vanadium and boron have also been proposed and can be used.

In any methanol synthesis process the reacted synthesis gas is cooled to the dewpoint of methanol and the methanol is condensed and separated. Heat is usually exchanged between reacted synthesis gas and cool unreacted synthesis gas (including recycled gas) but the balance of the exothermic heat of the synthesis reaction is available for any use that can be found for it. In particular it may be used to generate low-pressure or intermediate-pressure steam, or to heat a liquid (such as pressurised water), to be circulated as the heat source for one or more of the reboilers. Alternatively partly cooled reacted synthesis gas can itself be passed through the hot side of one or more of the reboilers.

A complete methanol production process includes also a synthesis gas generation section in which a carbonaceous feedstock such as natural gas, refinery off-gas, gaseous hydrocarbons, vaporisable liquid hydrocarbons, non-vaporisable hydrocarbons, coal or coke, is reacted with steam and possibly also carbon dioxide or oxygen. Depending on the hydrogen-to-carbon ratio of the feedstock and the extent to which reaction with oxygen is used, the generation section may involve a CO-shift and $CO_2$-removal stage. If carbon monoxide is available as a starting material, as in metallurgical off-gases, generation can begin with the shift stage. In synthesis gas generation gas streams are produced having temperatures over 400° C. and up to 1100° C. Heat recovery from such steam-containing raw synthesis gases by superheaters, boilers, boiler feed water heaters and preheaters for gas and air is widely practised. Low pressure steam from such recoveries or from the exhaust of steam let-down engines, or gas streams following one or more such heat recoveries are suitable for heating the column reboilers of the process of the invention, either by passing them through the hot side of the reboiler or (in the case of such gas streams) by exchanging them with a heating fluid such as pressurised water, with or without boiling, and passing such a fluid through the column reboilers.

The process of the invention is especially suitable in combination with a synthesis gas generation section in which $CO_2$ removal is incomplete or comprises catalytic reaction of gaseous or volatilisable hydrocarbon with steam without oxygen. Such a section produces a $CO_2$-containing gas from which a crude methanol containing 8–30% w/w of water results in methanol synthesis.

Figure 2:
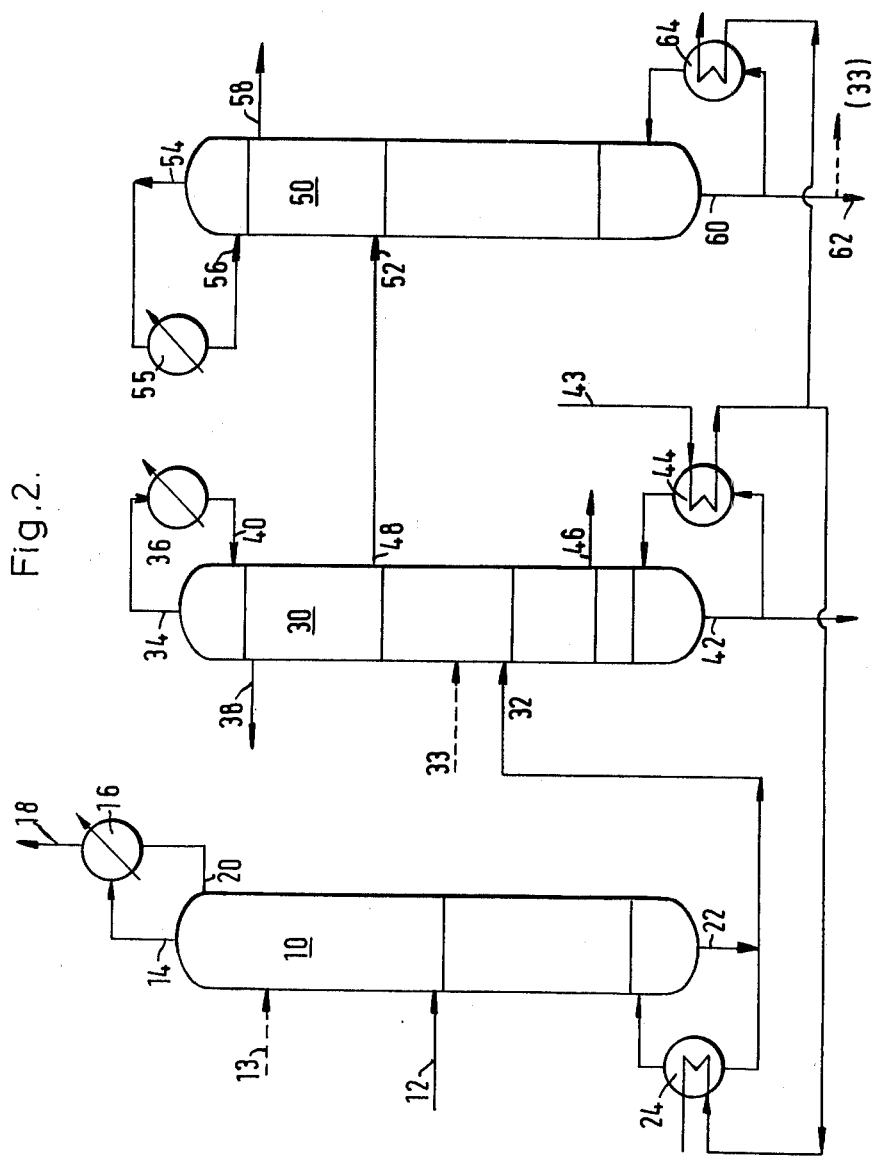
Figure 3:
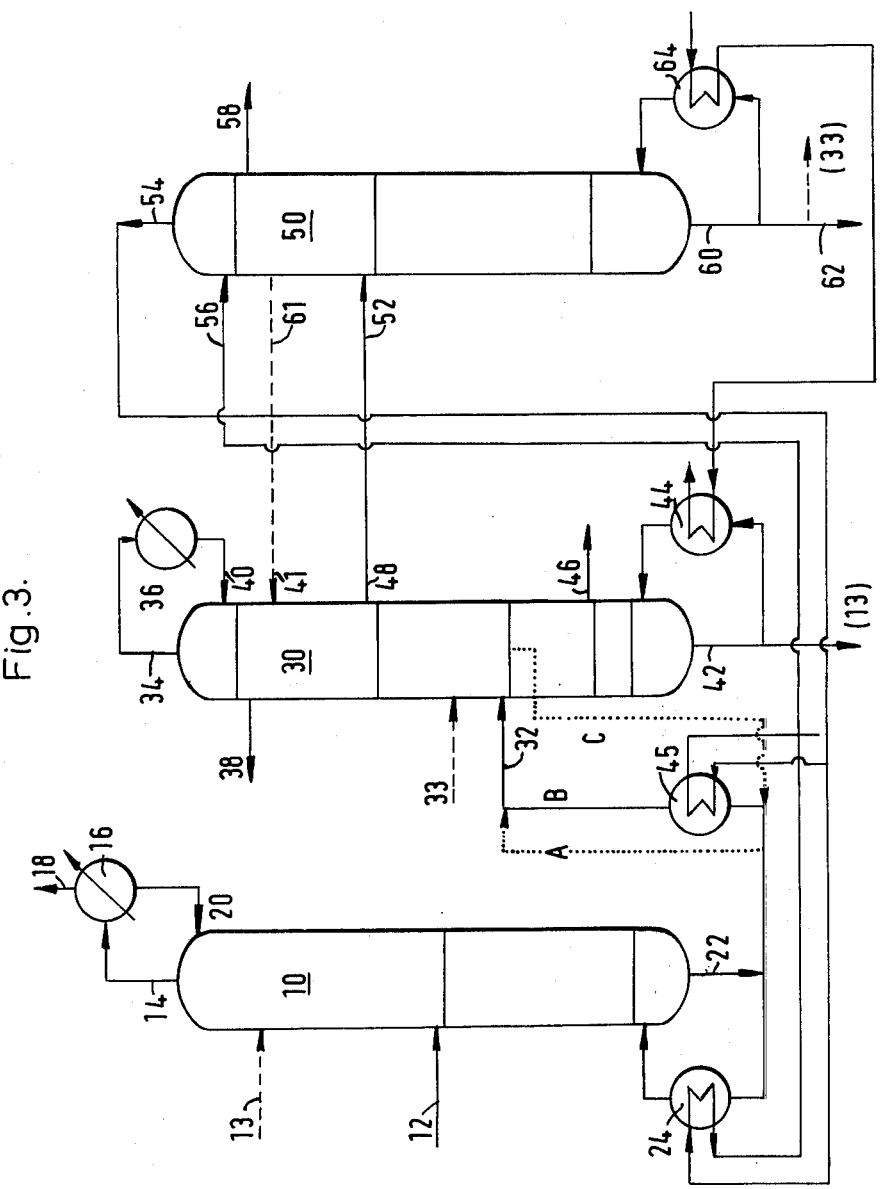

Three preferred forms of the invention are represented in the accompanying drawings, in which FIG. 1 represents a three-column process in which the last column is operated at high pressure and provides the heating fluid for the other two columns;

FIG. 2 represents a process in which all three columns are operated at low pressure; and FIG. 3 represents a process in which the last column is operated at a moderately increased pressure and its overhead vapour is heat exchanged with the feed to the middle column and the reboiler of the preliminary column.

It will be appreciated that minor features such as feed pumps, feed preheaters, vents and control valves are not shown. In the figures optional features are shown by pecked lines and alternative paths by dotted lines.

Referring to FIG. 1, preliminary "topping" column 10 receives its main feed of aqueous methanol at 12 and may, if desired, receive a feed of water at 13 if it is to operate in water-extractive conditions. Vapours of methanol and high-volatility impurities pass overhead at 14 and are cooled in condenser 16 to a temperature such that volatiles pass out at 18 but methanol is liquefied and flows back into the column at 20. The bottoms liquid passes out at 22 and is in part returned via reboiler 24 in heat exchange with pressurised methanol vapour from column 50 to be described and in part fed to column 30.

Column 30, the "first" column, receives its main feed (mislocated, as described above) at 32 and may, if desired, receive at 33 a feed of methanol, water and ethanol recycled from the bottoms of column 50. Methanol vapour passes overhead at 34 and is condensed at 36. Liquid methanol is divided into a product stream 38 and a reflux stream fed back into column 30 at 40. Column 30 may, if desired, receive at 41 a feed of methanol from column 50 in order to increase its reflux ratio. The bottoms liquid passing out at 42 consists substantially of water. It is in part heated in reboiler 44 by heat exchange with pressurized methanol vapour from column 50 to be described and in part discarded or, when column 10 is water-extractive, recycled to point 13. Column 30 includes also purge off-take 46, which is at the lower end of a region of the column in which, owing to mislocation of feed 32, the methanol to water ratio is substantially constant. The main off-take from column 30 is at 48, to provide the weakly aqueous methanol feed for column 50.

Column 50, the "second" column, separates the weakly aqueous methanol taken off at 48 from column 30 and now fed at 52. Methanol vapour passes overhead at 54 and is passed to the hot side of reboilers 44 and 24, where it condenses and provides (owing to its high pressure) the heat to maintain boiling in columns 30 and 10 respectively. The resulting liquid methanol is divided into a reflux stream fed to column 50 at 56 and a product stream 58 that is united with product stream 38 of column 30. The bottoms liquid of column 50 is taken out at 60 and is in part heated in reboiler 64 and in part discarded at 62 or, if desired, recycled to column 30 at 33. Reboiler 64 is heated by hot fluid from an external source, for example, by steam at 50 psig or process gas at 170° C. from elsewhere in the methanol production process or by a liquid heated by heat exchange with such a hot process gas.

Referring to FIG. 2, preliminary "topping" column 10 functions in the same way as in FIG. 1, except that in reboiler 24 the source of heat is process gas 43 that has been partly cooled in reboiler 44 of column 30 to be described. Column 30 also functions in the same way as in FIG. 1, except that in its reboiler 44 the source of heat is process gas at 150° C.; in reboiler 44 this gas is cooled to 125° C. and passed out to reboiler 24 and reboiler 64 to be described. Column 50 is at a lower pressure than in FIG. 1. It performs the same distillation operation as in FIG. 1, but differs in that (a) methanol vapour passing overhead is cooled and condensed by air-cooling or water-cooling at 55 to give the reflux stream fed back at 56 and (b) heating of reboiler 64 is by process gas that has been partly cooled in reboiler 44.

Referring to FIG. 3, this represents a process resembling that shown in FIG. 1, with the exceptions that (a) reboiler 44 of column 30 is heated by steam, which has been partly cooled in reboiler 64 of column 50;

(b) the vapour of methanol from the top 54 of column 50 is condensed not in reboiler 44 but in heat exchanger 45 and in the reboiler 24 of column 10. Heat exchanger 45 can be used in one of three ways. Following path B (full line) the feed, which is the bottoms of column 10, is partly vaporised and the resulting two-phase mixture is fed to column 30 at point 32. Following paths A and C the feed is not separately heated by heat exchange at 45 before it enters the column, but the mixture of feed and column liquid on the feed plate is withdrawn, heated in exchanger 45 and fed back to the plate. Following paths B and C, the liquid on the plate is withdrawn, mixed with the feed and the mixture is fed to the plate.

Table 1 sets out pressures, temperatures, compositions and flow rates that are common to the three processes specifically described.

TABLE 1

| Position | Theoretical Plate No. | Pressure psig | Temp. °C. | Composition, % w/w or ppm w/w (Flow rates kg mol h$^{-1}$) | | |
|---|---|---|---|---|---|---|
| | | | | Methanol | Water | Ethanol |
| Common to FIGS. 1 and 2 | | | | | | |
| 12 | 19 | 14 | 60 | 83 (73.4) | 17 (26.7) | 660 ppm |
| 22 | — | 14 | 86 | 82.98 | 17.02 | 660 ppm |
| 32 | 18 | 10 | 86 | (73.3) | (26.7) | |
| 34 | — | 3 | 70 | 100 | 0 | 0.1 ppm |
| 38 | 48 | — | — | 100 (28.86) | 0 | 0.1 ppm |
| 42(13) | — | 12 | 118 | 400 ppm | 100 (26.18) | 7 ppm |
| 46 | 5 | — | — | 54 | 44 | 1.96 |
| 48 | 30 | 6 | 74 | 99.7 (44.0) | 0.3 | 469 ppm |

Table 2 sets out the corresponding operating data that are special to each embodiment of the invention.

TABLE 2

| Position | Theoretical Plate No. | Pressure psig | Temp. °C. | Composition, % w/w or ppm w/w (Flow rates kg mol h$^{-1}$) | | |
|---|---|---|---|---|---|---|
| | | | | Methanol | Water | Ethanol |
| Special to FIG. 1 | | | | | | |
| 52 | 30 | 104 | 129 | 99.7 (44.0) | 0.3 | 469 ppm |
| 54 | — | 100 | 128 | 100 | 0 | 0.001 ppm |
| 58 | 48 | — | — | 100 (43.4) | 0 | 0.001 ppm |
| 60(33) | — | 110 | 133 | 87.9 (0.5) | 7.6 (0.08) | 4.5 (0.02) |
| Special to FIG. 2 | | | | | | |
| 52 | 30 | 6 | 73 | 99.7 (44.0) | 0.3 | 469 ppm |
| 54 | — | 3 | 70 | 100 | 0 | 0.001 ppm |
| 58 | 48 | — | — | 100 (43.4) | 0 | 0.001 ppm |
| 60 | — | 9 | 81 | 87.9 (0.5) | 7.6 (0.08) | 4.5 (0.02) |
| Special to FIG. 3 | | | | | | |
| 52 | 10 | 44 | 79 | 99.27 (46.066) | 0.6 (0.491) | 1300 ppm (0.0423) |
| 54 | — | 35.6 | 100 | 100 | 0 | 13 ppm |
| 32 | 10 | 10 | 94 | 84.93 (76.006) | 15.00 (23.8916) | 680 ppm (0.0424) |

Table 3 sets out the number of theoretical plates and the heat load for each of the three columns. (Note that the number of plates actually required is about double tha number of theoretical plates).

TABLE 3

| Column | No. of theoretical plates | | Heat load, metric ton calories per metric ton of product methanol | |
|---|---|---|---|---|
| 10 | 23 | (FIG. 1) | 150 | (from column 50 overhead) |
| | | (FIG. 2) | 150 | (from reboiler 44 at 85° C.) |
| | | (FIG. 3) | 110 | (from column 50 overhead) |
| 30 | 50* | (FIG. 1) | 450 | (from column 50 overhead) |
| | | (FIG. 2) | 300 | (external heat at 120°) |
| | | (FIG. 3) | 350 | (feed partly vaporised by column 50 overhead vapour) |
| | | | 220 | (external heat at 135° C.) |
| 50 | 50+ | (FIG. 1) | 600 | (external heat at 170°) |
| | | (FIG. 2) | 500 | (external reboiler 44 at 85° C.) |
| | 45 | (FIG. 3) | 470 | (external heat at 122° C.) |
| Total external heat load | | (FIG. 1) | 600 | |
| | | (FIG. 2) | 950 | |
| | | (FIG. 3) | 690 | |

*In view of the very low ethanol content of the product (0.1 ppm), much less than that (10 ppm) required by US Federal Specification Grade AA (OM232e, 20 July 1968), the number of plates in this column could be smaller and its bottoms temperature could be lower, thus affording better reboiler transfer from the overhead methanol vapour from column 50.
+Like column 30, this column could operate using fewer plates and still produce methanol meeting the Grade AA specification.

Although the total external heat load of the process of FIG. 2 is substantially higher than that of FIG. 1, it is the more economic process for use in combination with a methanol production process since it requires no source of heat as above 150° C. Both processes are thus preferably to to the common two-column process operated at 15 psig pressure and using steam to heat each column, the heat consumption of which is 960 metric ton calories per metric ton of product methanol.

The process of FIG. 3 is almost as economical as that of FIG. 2, but uses lower-grade external heat.

I claim:

1. A process for producing purified methanol by distillation, comprising the steps of:
   (a) feeding a water-methanol mixture containing small quantities of ethanol, ketones and higher alcohols to a first distillation column, taking a product methanol stream from an upper level, taking aqueous methanol containing at least 95% w/w of methanol as a side stream and taking a predominantly water stream as bottoms; and
   (b) feeding the aqueous methanol side stream to a second distillation column, taking a product methanol stream from an upper level and taking as bottoms a stream containing methanol, ethanol and water containing less than 40% w/w of water.

2. A process according to claim 1 in which the methanol-water feed is fed directly to the first column which includes an overhead off-take for components more volatile than methanol.

3. A process according to claim 1 in which the methanol-water feed is the bottoms of a preliminary distillation column in which components more volatile than methanol are taken overhead.

4. A process according to claim 1 in which each column is operated at a pressure in the range 1–20 psig, measured at the top and the columns are heated by passing fresh heat-carrying fluid to the first column reboiler and then passing the partly cooled fluid leaving that reboiler to the reboiler of the second column.

5. A process according to claim 1 in which the columns are heated by passing fresh heat-carrying fluid to the reboiler of the second column and passing methanol vapour from the top of that column in heat exchange with water-methanol mixture fed to the first column and the second column is operated at a pressure 20–70 psi higher than that of the columns to be heated by its overhead vapour.

6. A process according to claim 1 in which the first column side stream contains more than 99% w/w of methanol.

7. A process according to claim 1 in which the methanol flow rate of the first column side stream is 30–70% by mols of the methanol feed rate to that column.

8. A process according to claim 1 in which the water content of the second column bottoms stream is under 20% w/w.

9. A process according to claim 1 in which the starting crude methanol contains small quantities of ethanol, ketones and higher alcohols and these are taken off in a liquid purge stream from the first column at a level below the feed to this column.

10. A process according to claim 3 in which each column is operated at a pressure in the range 1 to 20 psig, measured at the top and the columns are heated by passing fresh heat-carrying fluid to the first column reboiler and then dividing the partly cooled fluid leaving said reboiler into two part-streams, passing one part-stream to the reboiler of the preliminary column and passing the other part-stream to the reboiler of the second column.

11. A process according to claim 1 in which
(i) the second column is operated at a pressure 70 to 120 psi higher than that of the first column and
(ii) the two columns are heated by passing fresh heat-carrying fluid to the reboiler of the second column and passing methanol vapour from the top of that column in heat exchange in the reboiler of the first column.

12. A process according to claim 3 in which
(i) the second column is operated at a pressure 70 to 120 psi higher than that of the first column and the preliminary column and
(ii) the three columns are heated by passing fresh heat-carrying fluid to the reboiler of the second column and passing vapour from the top of that column in heat exchange in the reboiler of the first column and the preliminary column.

13. In a process for producing purified methanol from a water and methanol mixture containing a small quantity of ethanol, ketones and higher alcohols by the steps of
(a) feeding said mixture to a first distillation column, taking a product methanol stream from an upper level, taking a predominantly water stream as bottoms and taking an aqueous methanol liquid side stream; and
(b) feeding said side stream to a second distillation column, taking a methanol stream at an upper level and taking a bottoms stream containing methanol, ethanol and water:
the improvement resulting in lowered heat consumption which comprises
(i) taking said aqueous methanol side stream from a level at which the liquid contains at least 95% w/w of methanol;
(ii) taking as said second column bottoms a stream containing less than 40% w/w of water; and
(iii) in said second distillation column taking a product methanol stream from an upper level.

14. A process according to claim 13, wherein the water content of said side stream is about 0.3 to 0.6% w/w.

* * * * *

UNITED STATES PATENT AND TRADEMARK OFFICE
CERTIFICATE OF CORRECTION

PATENT NO. : 4,210,495

DATED : July 1, 1980

INVENTOR(S) : Alwyn Pinto

It is certified that error appears in the above—identified patent and that said Letters Patent is hereby corrected as shown below:

IN THE HEADING

Section [30] After "March 11, 1977 [GB] United Kindgom .... 10403/77" add -- August 2, 1977 [GB] United Kingdom ....... 32399/77--.

Column 2, line 22, delete "not" and substitute therefore --hot--.

Column 3, line 7, delete "and".

Signed and Sealed this

Eighteenth Day of November 1980

[SEAL]

Attest:

SIDNEY A. DIAMOND

Attesting Officer

Commissioner of Patents and Trademark